(12) United States Patent
Sawado

(10) Patent No.: US 11,179,045 B2
(45) Date of Patent: Nov. 23, 2021

(54) BLOOD PRESSURE MEASUREMENT DEVICE AND BLOOD PRESSURE MEASUREMENT METHOD

(71) Applicant: SEIKO EPSON CORPORATION, Tokyo (JP)

(72) Inventor: Ayae Sawado, Kai (JP)

(73) Assignee: SEIKO EPSON CORPORATION, Tokyo (JP)

( * ) Notice: Subject to any disclaimer, the term of this patent is extended or adjusted under 35 U.S.C. 154(b) by 192 days.

(21) Appl. No.: 16/320,355

(22) PCT Filed: Jul. 21, 2017

(86) PCT No.: PCT/JP2017/026459
§ 371 (c)(1),
(2) Date: Jan. 24, 2019

(87) PCT Pub. No.: WO2018/021180
PCT Pub. Date: Feb. 1, 2018

(65) Prior Publication Data
US 2019/0261865 A1  Aug. 29, 2019

(30) Foreign Application Priority Data
Jul. 25, 2016 (JP) .............................. JP2016-145455

(51) Int. Cl.
*A61B 5/0205* (2006.01)
*A61B 5/11* (2006.01)
(Continued)

(52) U.S. Cl.
CPC .............. *A61B 5/0205* (2013.01); *A61B 5/02* (2013.01); *A61B 5/11* (2013.01); *A61B 5/4809* (2013.01);
(Continued)

(58) Field of Classification Search
CPC ........... A61B 5/0205; A61B 5/02; A61B 5/11; A61B 5/4809; A61B 5/746;
(Continued)

(56) References Cited

U.S. PATENT DOCUMENTS 5,606,977 A  *  3/1997  Ramsey, III ....... A61B 5/02225
                                                600/494
7,455,643 B1 * 11/2008  Li .......................... A61B 5/021
                                                600/490
(Continued)

FOREIGN PATENT DOCUMENTS

EP        2 679 256 A1    1/2014
JP      H08-280640 A     10/1996
(Continued)

OTHER PUBLICATIONS

Aug. 29, 2017 International Search Report issued in International Patent Application No. PCT/JP2017/026459.

*Primary Examiner* — Gary Jackson
*Assistant Examiner* — Sebastian X Lukjan
(74) *Attorney, Agent, or Firm* — Oliff PLC

(57) ABSTRACT

A blood pressure measurement device including a measurement wave detection unit that detects a measurement wave that passed through a measurement region of a subject and generates a detection signal, a blood pressure analysis unit that repeatedly identifies a blood pressure of the subject by analyzing the detection signal, a state determination unit that determines whether or not the subject is in a sleep state, a change determination unit that determines whether or not a time change rate of the blood pressure exceeds a threshold value, and a measurement control unit that shortens a time interval where the blood pressure analysis unit identifies the blood pressure in a case where the state determination unit determines that the subject is in the sleep state and the (Continued)

change determination unit determines that the time change rate exceeds the threshold value.

13 Claims, 6 Drawing Sheets

(51) Int. Cl.
*A61B 5/00* (2006.01)
*A61B 5/02* (2006.01)
*A61B 5/021* (2006.01)
*A61B 5/024* (2006.01)

(52) U.S. Cl.
CPC .............. *A61B 5/746* (2013.01); *A61B 5/024* (2013.01); *A61B 5/02108* (2013.01); *A61B 2560/0252* (2013.01); *A61B 2562/029* (2013.01)

(58) Field of Classification Search
CPC ................ A61B 5/02108; A61B 5/024; A61B 2560/0252; A61B 2562/029; A61B 5/0261; A61B 5/02416; A61B 5/02116; A61B 5/681; A61B 2560/0242
See application file for complete search history.

(56) References Cited

U.S. PATENT DOCUMENTS

| | | | | |
|---|---|---|---|---|
| 2012/0143068 | A1* | 6/2012 | Cheng | G16H 40/63 600/485 |
| 2014/0278139 | A1* | 9/2014 | Hong | A61B 5/7264 702/19 |
| 2015/0164351 | A1* | 6/2015 | He | H05B 47/105 702/19 |
| 2015/0182160 | A1* | 7/2015 | Kim | A61B 5/742 600/301 |
| 2015/0374310 | A1* | 12/2015 | Lee | A61B 5/7285 600/483 |

FOREIGN PATENT DOCUMENTS

| | | |
|---|---|---|
| JP | 2001-070260 A | 3/2001 |
| JP | 2010-099383 A | 5/2010 |
| JP | 2013-248364 A | 12/2013 |
| JP | 2015-146847 A | 8/2015 |
| JP | 2015-154884 A | 8/2015 |
| JP | 2016-064125 A | 4/2016 |
| JP | 2016-101222 A | 6/2016 |
| JP | 2016-107095 A | 6/2016 |
| WO | 2012/114514 A1 | 8/2012 |

* cited by examiner

[Fig. 1]
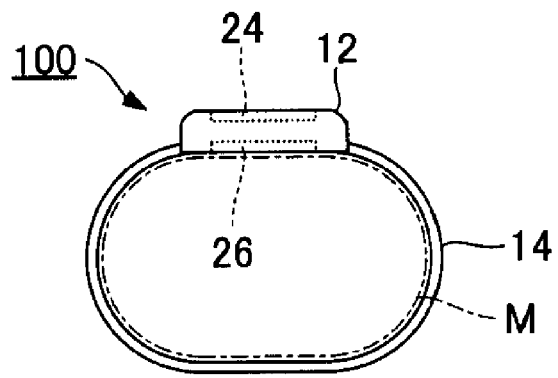
[Fig. 2]
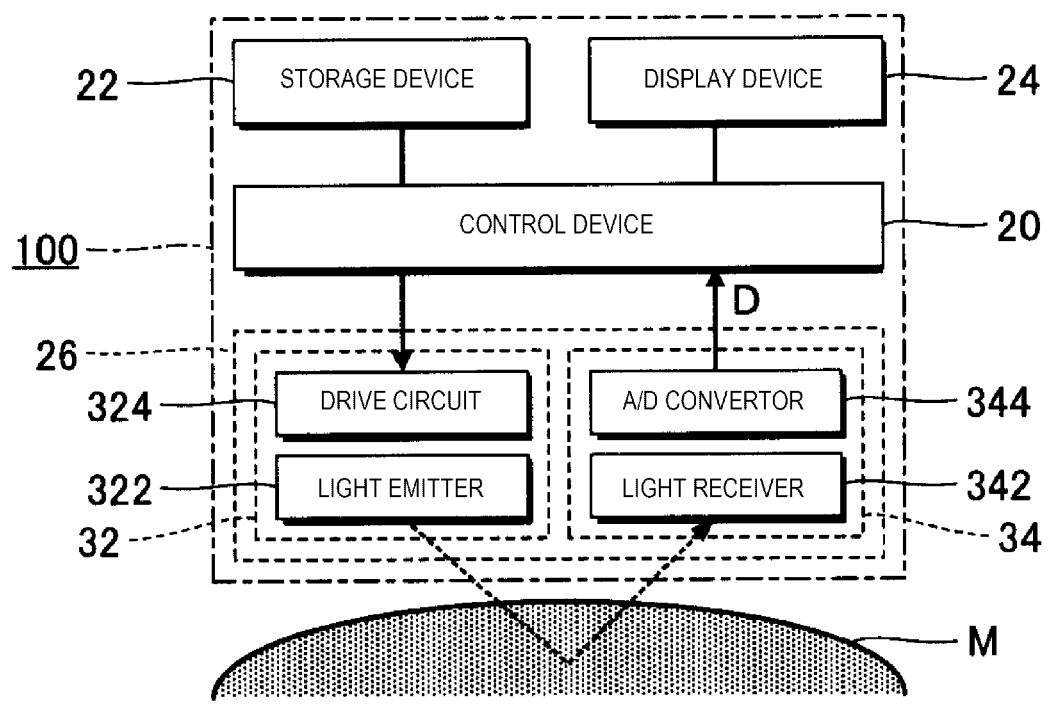

[Fig. 3]
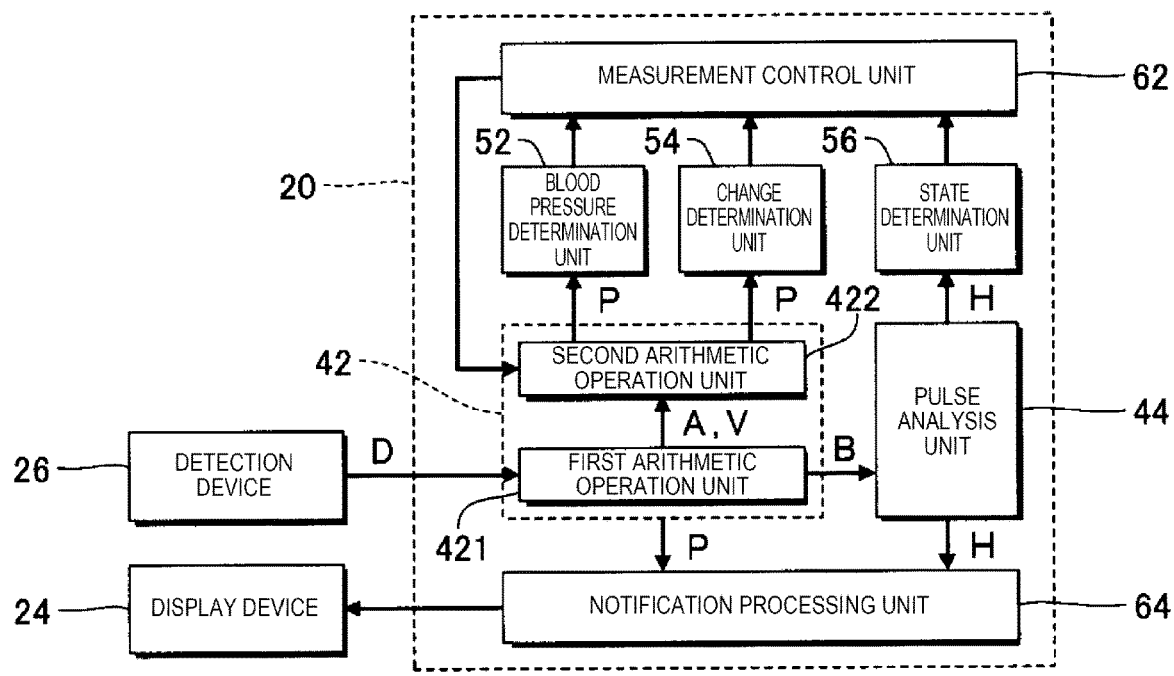
[Fig. 4]
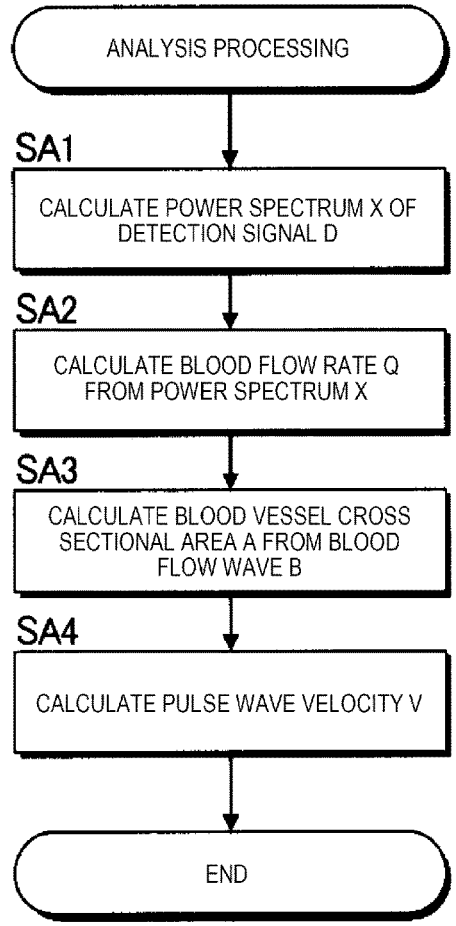

[Fig. 5]
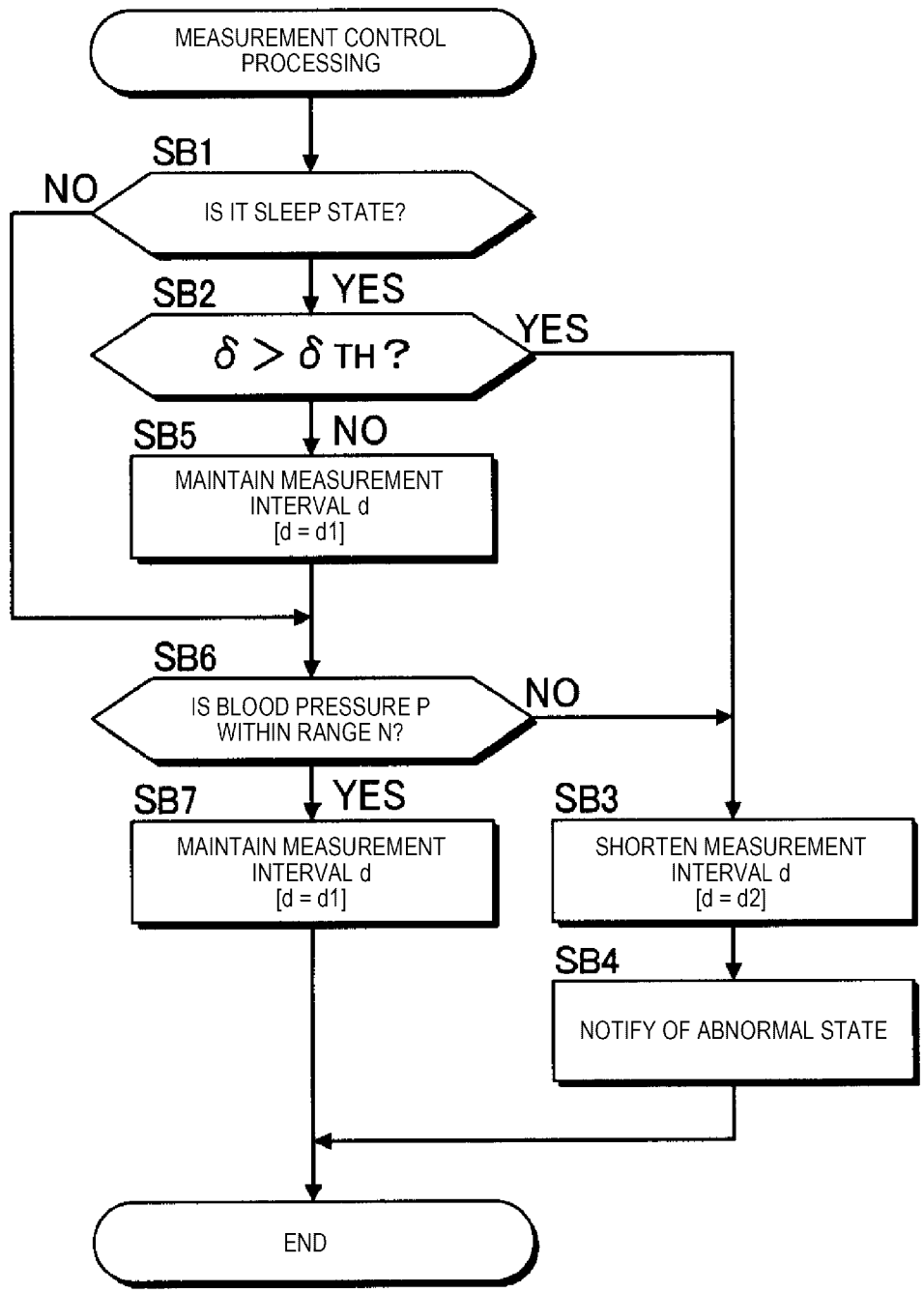

[Fig. 6]
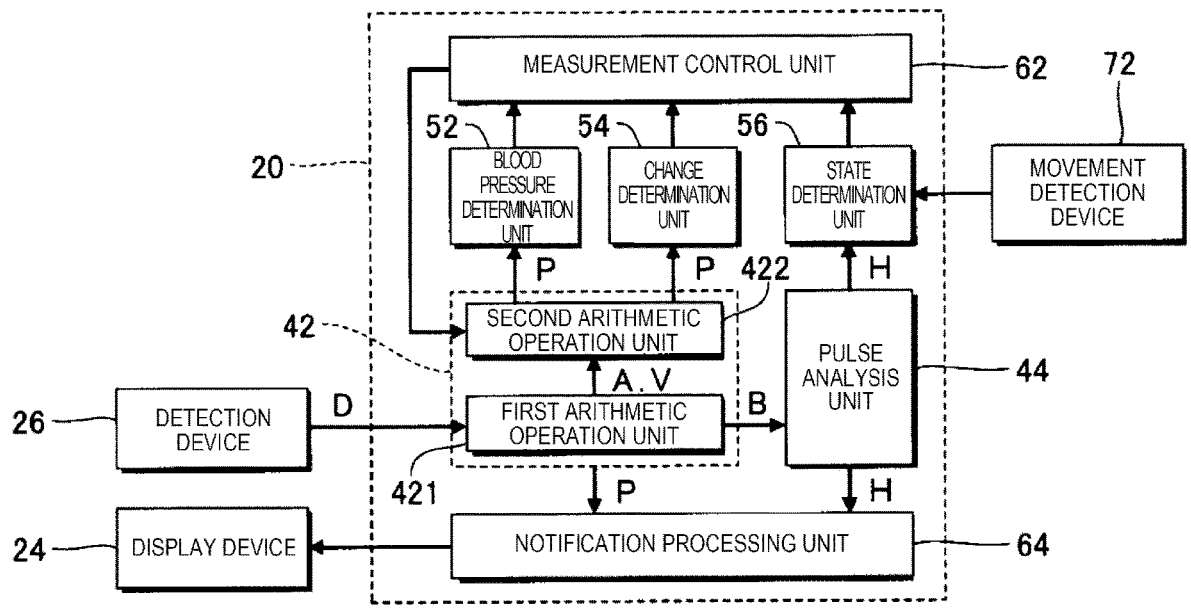
[Fig. 7]
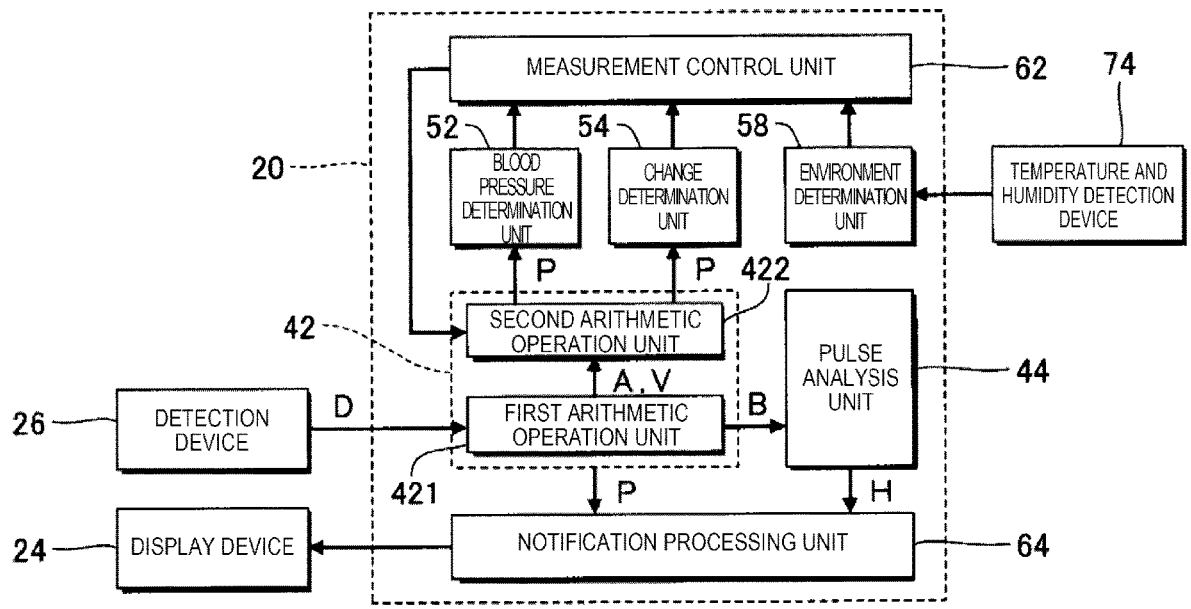

[Fig. 8]
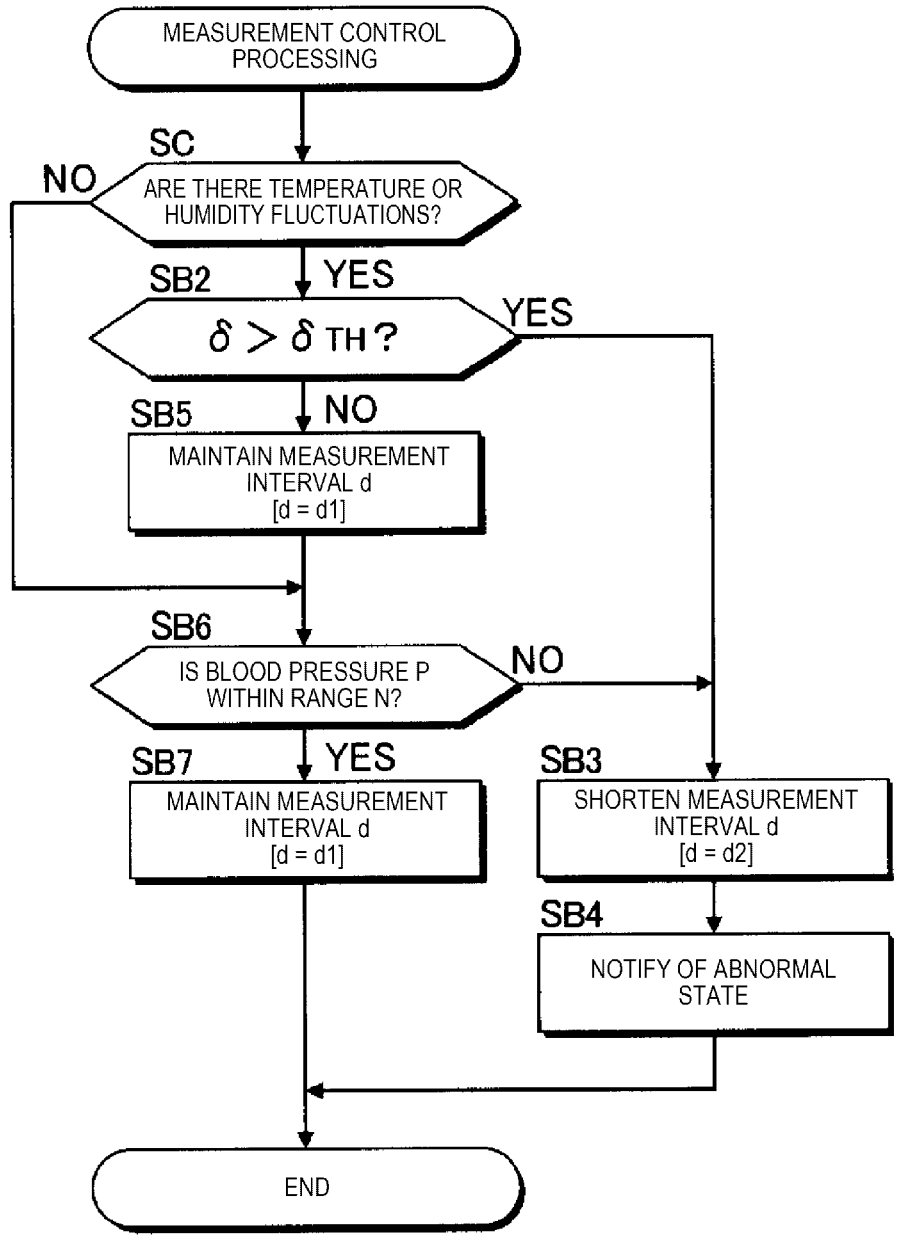

[Fig. 9]
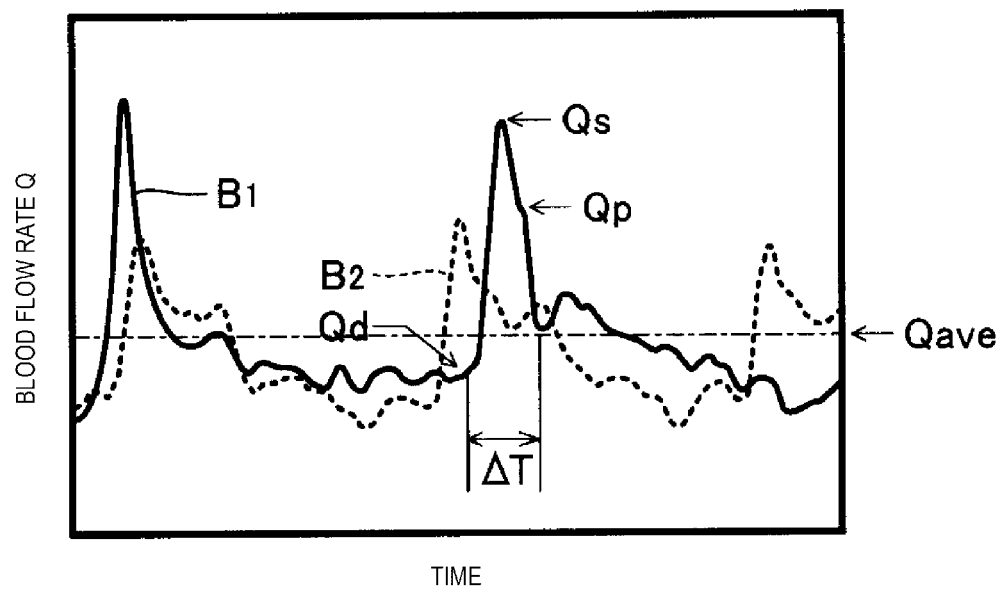

BLOOD PRESSURE MEASUREMENT DEVICE AND BLOOD PRESSURE MEASUREMENT METHOD

TECHNICAL FIELD

The present invention relates to a technology for measuring a blood pressure.

BACKGROUND ART

Various technologies for measuring biological information of a subject have been proposed in the related art. For example, PTL 1 discloses a configuration in which a sleep period of a subject is identified from a detection result of a body movement using an acceleration sensor and a detection result of a body temperature using a temperature sensor, and a blood pressure measurement using a cuff attached to the wrist of the subject is performed before and after the sleep period.

CITATION LIST

Patent Literature

PTL 1: JP-A-2010-99383

SUMMARY OF INVENTION

Technical Problem

According to the technology of PTL 1, since the subject needs to sleep while attaching the cuff, sleep may be disturbed by pressurization or depressurization of the cuff at the time of the blood pressure measurement. In the technology of PTL 1, blood pressure is measured only before and after the sleep period. Therefore, there is a problem that it is not possible to appropriately detect a blood pressure fluctuation which may cause a stroke or a heart disease such as an abnormal rise in the blood pressure due to the abnormal rise in the blood pressure in a sleep state (nocturnal hypertension) and change of an environmental temperature. In consideration of the above circumstances, the present invention aims to appropriately detect the blood pressure fluctuation in a situation where the blood pressure fluctuation tends to occur while suppressing a load on the subject.

Solution to Problem

According to a first aspect of the present invention, to solve the above problem, there is provided a blood pressure measurement device including a measurement wave detection unit that detects a measurement wave that passed through a measurement region of a subject and generates a detection signal, a blood pressure analysis unit that repeatedly identifies a blood pressure of the subject by analyzing the detection signal, a state determination unit that determines whether or not the subject is in a sleep state, a change determination unit that determines whether or not a time change rate of the blood pressure exceeds a threshold value, and a measurement control unit that shortens a time interval where the blood pressure analysis unit identifies the blood pressure in a case where the state determination unit determines that the subject is in the sleep state and the change determination unit determines that the time change rate exceeds the threshold value. With the above configuration, since the blood pressure is identified by analyzing the detection signal in which the measurement wave that passed through the measurement region of the subject is detected, it is possible to reduce a physical load of the subject compared with the technology of PTL 1 that uses a cuff to measure blood pressure. In addition, since the time interval of the blood pressure measurement is shortened when the time change rate exceeds the threshold value in the sleep state, it is possible to appropriately detect the blood pressure fluctuation in a situation where there is a possibility that a health condition of the subject is abnormal.

The blood pressure measurement device according to a preferred aspect of the present invention includes a pulse analysis unit that identifies a pulse rate according to the detection signal, and the state determination unit determines whether or not the subject is in the sleep state according to the pulse rate. With the above aspect, since it is determined whether or not the subject is in the sleep state according to the pulse rate identified from the detection signal, there is an advantage that a device configuration is simplified as compared with a configuration in which an element separate from the detection of the measurement wave is used for a determination of the active state of the subject. The blood pressure measurement device according to another aspect of the present invention includes a movement detection unit that detects a movement of the subject, and the state determination unit determines whether or not the subject is in the sleep state according to the detection result by the movement detection unit.

According to a second aspect of the present invention, there is provided a blood pressure measurement device including a measurement wave detection unit that detects a measurement wave that passed through a measurement region of a subject and generates a detection signal, a blood pressure analysis unit that repeatedly identifies a blood pressure of the subject by analyzing the detection signal, an environment determination unit that determines whether there is a change in temperature or humidity of a measurement environment in which the subject is present, a change determination unit that determines whether or not a time change rate of the blood pressure exceeds a threshold value, and a measurement control unit that shortens a time interval where the blood pressure analysis unit identifies the blood pressure in a case where the environment determination unit determines that there is a change in the temperature or humidity of the measurement environment and the change determination unit determines that the time change rate exceeds the threshold value. With the above configuration, since the blood pressure is identified by analyzing the detection signal in which the measurement wave that passed through the measurement region of the subject is detected, it is possible to reduce a physical load of the subject compared with the technology of PTL 1 that uses a cuff to measure blood pressure. In addition, since the time interval of the blood pressure measurement is shortened when the temperature or humidity of the measurement environment fluctuates, it is possible to appropriately detect the blood pressure fluctuation in a situation where there is a high possibility of fluctuation in the blood pressure of the subject.

The blood pressure measurement device according to the first aspect or the second aspect of the present invention includes a blood pressure determination unit that determines whether or not the blood pressure is in a normal range, and the measurement control unit shortens the time interval where the blood pressure analysis unit identifies the blood pressure in a case where the blood pressure determination unit determines that the blood pressure is not within the normal range. With the above aspect, since the time interval of the blood pressure measurement is shortened even when the blood pressure of the subject is not within the normal range, the above mentioned effect that the blood pressure fluctuation may be appropriately detected is especially remarkable. Furthermore, according to the configuration including a notification processing unit for notifying of an abnormal state of the subject when the blood pressure determination unit determines that the blood pressure is not within the normal range, it may be possible to grasp an abnormality of the subject at an early stage.

BRIEF DESCRIPTION OF DRAWINGS

FIG. 1 is a side view of a blood pressure measurement device according to a first embodiment of the present invention.

FIG. 2 is a configuration diagram of the blood pressure measurement device.

FIG. 3 is a configuration diagram focused on a function of the blood pressure measurement device.

FIG. 4 is a flowchart of an analysis processing.

FIG. 5 is a flowchart of a measurement control processing.

FIG. 6 is a configuration diagram focused on a function of a blood pressure measurement device in a second embodiment.

FIG. 7 is a configuration diagram focused on a function of a blood pressure measurement device in a third embodiment.

FIG. 8 is a flowchart of a measurement control processing in the third embodiment.

FIG. 9 is a waveform diagram of a blood flow wave in a normal temperature environment and a low temperature environment.

DESCRIPTION OF EMBODIMENTS

First Embodiment

FIG. 1 is a side view of a blood pressure measurement device 100 according to a first embodiment of the present invention. The blood pressure measurement device 100 of the first embodiment is a measuring equipment that noninvasively measures a blood pressure of a subject and is attached to a region M of the body of the subject to be measured (hereinafter referred to as "measurement region"). The blood pressure measurement device 100 of the first embodiment is a wristwatch type portable equipment including a casing unit 12 and a belt 14, and is able to be attached to a wrist of the subject by winding the belt 14 around the wrist, which is an example of the measurement region M.

FIG. 2 is a configuration diagram of the blood pressure measurement device 100. As illustrated in FIG. 2, the blood pressure measurement device 100 of the first embodiment includes a control device 20, a storage device 22, a display device 24, and a detection device 26. The control device 20 and the storage device 22 are installed inside the casing unit 12. As illustrated in FIG. 1, the display device 24 (for example, a liquid crystal display panel) is installed on a surface of the casing unit 12 (for example, the surface opposite to the measurement region M), and displays various images including measurement results under control of the control device 20. Note that, in the blood pressure measurement device 100, an operation equipment for receiving an operation from a user (for example, a subject or a measurer) is also installed, however in FIG. 1 and FIG. 2, illustration is omitted for the sake of convenience.

The detection device 26 in FIG. 2 is a sensor module for generating a detection signal D according to a state of the measurement region M, and is installed, for example, on the surface of the casing unit 12 facing the measurement region M. As illustrated in FIG. 2, the detection device 26 of the first embodiment includes an irradiation unit 32, and a detection unit 34.

The irradiation unit 32 irradiates the measurement region M with light. The irradiation unit 32 of the first embodiment includes a light emitter 322 and a drive circuit 324. The light emitter 322 is a light source that emits a light of a predetermined wavelength (for example, 850 nm) to the measurement region M. For example, a vertical cavity surface emitting laser (VCSEL) that emits a coherent laser light in a narrow bandwidth by resonance in the resonator is suitably used as the light emitter 322. Note that, a wavelength of the light emitted from the light emitter 322 is arbitrary. The drive circuit 324 causes the light emitter 322 to emit the light by supplying a drive current according to an instruction from the control device 20.

The light emitted from the irradiation unit 32 (light emitter 322) enters the measurement region M, and is reflected and scattered inside the measurement region M. The light that passed through inside of the measurement region M is emitted to the casing unit 12 side and reaches the detection unit 34. The detection unit 34 (an example of a measurement wave detection unit) detects the light that passed through the measurement region M and generates a detection signal D. As understood from the above description, the detection device 26 of the first embodiment is a reflection type optical sensor in which the irradiation unit 32 and the detection unit 34 are located on one side with respect to the measurement region M. As illustrated in FIG. 2, the detection unit 34 of the first embodiment includes a light receiver 342 and an A/D converter 344.

The light receiver 342 is configured with, for example, a photodiode (PD), and generates a detection signal D according to a received light level of the light arriving from the measurement region M. Since an amount of the light absorbed by blood in a blood vessel is different between a time of expansion and a time of contraction, the detection signal D generated by the light receiver 342 according to the light receiving level from the measurement region M is a pulse wave signal including periodic fluctuation component corresponding to a pulsation component of artery inside the measurement region M. The A/D converter 344 converts the detection signal D generated by the light receiver 342 from analog to digital.

The control device 20 in FIG. 2 is an arithmetic operation processing device such as a central processing unit (CPU) or field-programmable gate array (FPGA), and controls the entire blood pressure measurement device 100. The storage device 22 is configured with, for example, a nonvolatile semiconductor memory, and stores a program executed by the control device 20 and various data used by the control device 20. Although the control device 20 and the storage device 22 are illustrated as separate elements in FIG. 2, it is also possible to realize the control device 20 including the storage device 22 by application specific integrated circuit (ASIC) or the like, for example.

FIG. 3 is a configuration diagram focused on a function of the blood pressure measurement device 100. As illustrated in FIG. 3, the control device 20 of the first embodiment executes a program stored in the storage device 22, and realizes a plurality of functions (blood pressure analysis unit 42, pulse analysis unit 44, blood pressure determination unit 52, change determination unit 54, state determination unit 56, measurement control unit 62, notification processing unit 64) for measuring the blood pressure of the subject. Note that, a configuration in which the functions of the control device 20 are distributed to a plurality of integrated circuits, or a configuration in which a portion or all of the functions of the control device 20 is realized by dedicated electronic circuits can be adopted.

The blood pressure analysis unit 42 identifies the blood pressure P of the subject by analyzing the detection signal D generated by the detection device 26 (detection unit 34). The identification of the blood pressure P by the blood pressure analysis unit 42 is repeatedly executed at a time interval d (hereinafter referred to as "measurement interval"). The measurement interval d is a cycle for analyzing the blood pressure P of the subject, and is set to a sufficiently long interval (for example, several minutes) for one cycle of the pulse, for example.

As illustrated in FIG. 3, the blood pressure analysis unit 42 of the first embodiment includes a first arithmetic operation unit 421 and a second arithmetic operation unit 422. The first arithmetic operation unit 421 calculates a blood vessel cross sectional area A and a pulse wave velocity V of the subject. FIG. 4 is a flowchart of a processing in which the first arithmetic operation unit 421 calculates the blood vessel cross sectional area A and the pulse wave velocity V (hereinafter referred to as "analysis processing"). For example, the analysis processing of FIG. 4 is executed at a sufficiently short interval with respect to one cycle of the pulse (therefore, a sufficiently short interval as compared with the measurement interval d).

Upon starting the analysis processing, the first arithmetic operation unit 421 calculates a power spectrum X of the detection signal D generated by the detection unit 34 (SA1). For the calculation of the power spectrum X of the detection signal D, for example, a frequency analysis such as fast Fourier transformation is used. In the detection signal D, a section to be calculated for the power spectrum X moves in a direction of a time axis for each analysis processing.

The first arithmetic operation unit 421 calculates a blood flow rate Q from the power spectrum X of the detection signal D (SA2). Specifically, the first arithmetic operation unit 421 calculates the blood flow rate Q by, for example, an arithmetic operation of the following equation (1) to which the power spectrum X is applied. A symbol K in the equation (1) is a predetermined constant, and the symbol <I$^2$> means a total power of the detection signal D. Symbols f1 and f2 mean predetermined cutoff frequencies, and a symbol f means a frequency of the light (laser light) irradiated by the irradiation unit 32.

[Equation 1]

$$Q = \frac{K \int_{f_1}^{f_2} f \cdot X df}{\langle I^2 \rangle} \quad (1)$$

The first arithmetic operation unit 421 calculates the blood vessel cross sectional area A from a time series B of the blood flow rate Q (hereinafter referred to as "blood flow wave") (SA3). The blood flow wave B means a time change of the blood flow rate Q. Further, the first arithmetic operation unit 421 calculates the pulse wave velocity V (PWV) by differentiating the blood flow rate Q with the blood vessel cross sectional area A (SA4). A specific example of the analysis processing by the first arithmetic operation unit 421 is as described above. A method of calculating the blood flow rate Q, the blood vessel cross sectional area A, and the pulse wave velocity V of the subject is not limited to the above examples.

The second arithmetic operation unit 422 in FIG. 3 sequentially calculates the blood pressure P of the subject at the measurement interval d. The blood pressure P is a systolic blood pressure (maximum blood pressure) or a diastolic blood pressure (minimum blood pressure). The second arithmetic operation unit 422 of the first embodiment sequentially calculates the blood pressure P for each measurement interval d using the results of arithmetic operation by the first arithmetic operation unit 421 (blood vessel cross sectional area A and pulse wave velocity V). Specifically, it is possible to calculate the blood pressure P by the arithmetic operation of the following equation (2) applying the blood vessel cross sectional area A and the pulse wave velocity V calculated by the first arithmetic operation unit 421. Note that, a symbol p in the equation (2) means an average arterial pressure, a symbol a means a time average of the blood vessel cross sectional area A. In addition, a symbol ρ is a mass density of the blood and is set to a predetermined value.

[Equation 2]

$$P = p + \rho V^2 \frac{A-a}{a} \quad (2)$$

The pulse analysis unit 44 in FIG. 3 identifies a pulse rate H (the number of pulses per unit time) of the subject. Specifically, the pulse analysis unit 44 identifies the pulse rate H by analyzing the blood flow wave B calculated (SA3) by the first arithmetic operation unit 421. The identification of the pulse rate H by the pulse analysis unit 44 is sequentially executed for each measurement interval d in synchronization with the identification of the blood pressure P by the blood pressure analysis unit 42, for example.

The blood pressure determination unit 52 determines whether or not the blood pressure P identified by the blood pressure analysis unit 42 is within a predetermined range (hereinafter referred to as "normal range") N or not. The normal range N means the range of the blood pressure P that can be diagnosed that there is no abnormality in a health condition of the subject. Further, the change determination unit 54 determines whether or not the time change rate (the absolute value of a change amount of the blood pressure P per unit time) δ of the blood pressure P identified by the blood pressure analysis unit 42 exceeds a predetermined threshold value δTH.

The state determination unit 56 determines an active state (sleep state, awake state) of the subject. Specifically, the state determination unit 56 determines whether or not the subject is in the sleep state. The state determination unit 56 of the first embodiment determines whether or not the subject is in the sleep state according to the pulse rate H identified by the pulse analysis unit 44. Specifically, the state determination unit 56 determines that the subject is in the sleep state when the pulse rate H is stably maintained at a numerical value below the predetermined threshold value, and determines that the subject is in an awake state when the pulse rate H is maintained at a numerical value exceeding the threshold value or dynamically fluctuates.

The measurement control unit 62 in FIG. 3 variably controls the measurement interval d of the blood pressure P by the blood pressure analysis unit 42. The measurement control unit 62 of the first embodiment variably controls the measurement interval d according to the determination result of each of the blood pressure determination unit 52, the change determination unit 54, and the state determination unit 56. In a situation where the health condition of the subject is abnormal, it is desirable to raise a measurement frequency of the blood pressure P as compared with a situation where the health condition is normal. In consideration of the above circumstances, the measurement control unit 62 of the first embodiment increases the measurement frequency of the blood pressure P by shortening the measurement interval d when it is estimated that the health condition of the subject is abnormal. That is, a temporal resolution of the blood pressure measurement is improved.

For example, in a situation where the subject is in the sleep state, if the health condition is normal, the possibility that the blood pressure P suddenly fluctuates is low. Therefore, when the blood pressure P suddenly fluctuates in the sleep state, there is a possibility that an abnormality such as nocturnal hypertension is occurring in the subject. In consideration of the above tendency, in the first embodiment, the measurement control unit 62 shortens the measurement interval d in a case where the state determination unit 56 determines that the subject is in the sleep state and the change determination unit 54 determines that the time change rate δ of the blood pressure P exceeds the threshold value δTH (that is, the blood pressure P suddenly fluctuates). The measurement control unit 62 also shortens the measurement interval d in a case where the blood pressure P of the subject in the awake state is outside the normal range N, since it is assumed that the health condition of the subject is abnormal.

The notification processing unit 64 in FIG. 3 notifies a user (for example, a subject or a measurer) of information such as the measurement result. Specifically, the notification processing unit 64 causes the display device 24 to display the blood pressure P identified by the blood pressure analysis unit 42 and the pulse rate H identified by the pulse analysis unit 44. In addition, the notification processing unit 64 of the first embodiment notifies the user that the health condition of the subject is abnormal (hereinafter referred to as "abnormal state"). Specifically, when the blood pressure P of the subject in the sleep state suddenly fluctuates, or when the blood pressure P of the subject is outside the normal range N, the notification processing unit 64 causes the display device 24 to display a warning of an abnormal state by a message such as "abnormal blood pressure is detected, please consult at a medical institution", for example. Note that, a method of notifying the user of the measurement result and the abnormal state is not limited to an image display. For example, it is also possible to notify the user of the measurement result and the abnormal state using a voice.

FIG. 5 is a flowchart of a processing for controlling the measurement interval d of the blood pressure P of the subject (hereinafter referred to as "measurement control processing"). The measurement control processing in FIG. 5 is repeatedly executed with an interruption occurring at an interval shorter than the measurement interval d as a trigger.

When the measurement control processing is started, the state determination unit 56 determines whether or not the subject is in the sleep state (SB1). When the state determination unit 56 determines that the subject is in the sleep state (SB1: YES), the change determination unit 54 determines whether or not the time change rate δ of the blood pressure P of the subject exceeds the threshold value δTH (SB2). When the state determination unit 56 determines that the subject is in the sleep state (SB1: YES) and the change determination unit 54 determines that the time change rate δ exceeds the threshold value δTH (SB2: YES), there is a possibility that an abnormality such as nocturnal hypertension may occur in the subject. The measurement control unit 62 shortens the measurement interval d of the blood pressure P by the blood pressure analysis unit 42 (SB3). Specifically, the measurement control unit 62 sets the measurement interval d to a shorter interval d2 by comparing with a predetermined standard interval d1. The standard interval d1 is a standard interval suitable for the blood pressure measurement of the subject in a healthy condition, and is set to, for example, a time length of about 15 minutes to 30 minutes. On the other hand, the interval d2 after shortening is an interval suitable for the blood pressure measurement of the subject having an abnormal health condition, for example, set to the time length of about 5 minutes. In addition, the notification processing unit 64 notifies the user of the abnormal state by causing the display device 24 to display the warning (SB4). On the other hand, when the time change rate δ of the blood pressure P is lower than the threshold value δTH (SB2: NO), the measurement interval d is set to the standard interval d1 (SB5).

When the subject is not in the sleep state (SB1: NO) or when the time change rate δ is lower than the threshold value δTH (SB2: NO, SB5), the blood pressure determination unit 52 determines whether or not the blood pressure P of the subject is within the normal range N (SB6). When the blood pressure determination unit 52 determines that the blood pressure P is not within the normal range N (SB6: NO), the measurement control unit 62, in the same way as when the time change rate δ increases in the sleep state (SB2: YES) the measurement interval d is shortened to the interval d2 (SB3). That is, when the subject is in the awake state (SB1: NO), even if the time change rate δ of the blood pressure P fluctuates due to an exercise or the like, for example, the measurement interval d is maintained as the normal state at the standard interval d1, and the measurement interval d is shortened to the interval d2 when the blood pressure P changes to a numerical value outside the normal range N. In addition, the notification processing unit 64 notifies the user of the abnormal state (abnormality of the blood pressure P) by causing the display device 24 to display the warning (SB4). On the other hand, when the blood pressure determination unit 52 determines that the blood pressure P is within the normal range N (SB6: YES), the measurement interval d is set to the standard interval d1 (SB7).

With the above configuration, in the first embodiment, since the blood pressure P is identified by analyzing the detection signal D in which the light that passed through the measurement region M of the subject is detected, it is possible to reduce a physical load of the subject compared with the technology of PTL 1 that uses a cuff to measure the blood pressure. For example, it is possible to continuously measure the blood pressure P without disturbing the sleep of the subject. When it is estimated that the blood pressure P of the subject is abnormal, the measurement interval d of the blood pressure P is shortened. Specifically, the measurement interval d is shortened when the time change rate δ exceeds the threshold value δTH in the sleep state (for example, nocturnal hypertension is estimated). Therefore, it is possible to appropriately detect the blood pressure fluctuation in a situation where there is a possibility that the health condition of the subject is abnormal. Further, compared with a configuration in which the blood pressure P is identified at the interval d2 irrespective of the condition of the subject, there is an advantage that a processing load of the control device 20 (in particular, the blood pressure analysis unit 42) is reduced. Since the blood pressure measurement device 100 of the first embodiment is a compact portable device, the battery capacity is limited. Therefore, the first embodiment in which a power consumption is reduced by reducing the processing load is particularly effective.

Furthermore, in the first embodiment, since the measurement interval d is shortened also when the blood pressure P is not within the normal range N, an effect that the blood pressure fluctuation can be appropriately detected in a situation where there is a possibility that the health condition of the subject is abnormal, is especially remarkable. When the time change rate δ of the blood pressure P exceeds the threshold value δTH in the sleep state and when the blood pressure P is not within the normal range N, the abnormal state of the subject is notified. Therefore, it is possible to grasp the abnormal state of the subject at an early stage and to perform measures for improvement (for example, visit a medical institution).

In the first embodiment, whether or not the subject is in the sleep state is determined according to the pulse rate H identified from the detection signal D. That is, the detection device 26 is also used for determining the active state of the subject and identifying the blood pressure P. Therefore, there is an advantage that the configuration of the blood pressure measurement device 100 is simplified as compared with a configuration in which an element separate from the detection device 26 is used for determining the active state of the subject.

Second Embodiment

A second embodiment of the present invention will be described. Note that, in each of the embodiments exemplified below, elements having the same effects or functions as those of the first embodiment are denoted by the same reference numerals used in the description of the first embodiment, and detailed description thereof will be appropriately omitted.

FIG. 6 is a configuration diagram focused on a function of a blood pressure measurement device 100 in a second embodiment. As illustrated in FIG. 6, the blood pressure measurement device 100 of the second embodiment has a configuration in which a movement detection device 72 is added to the same element as in the first embodiment. The movement detection device 72 (an example of the movement detection unit) is a body movement sensor that detects a movement of a subject. For example, an acceleration sensor for detecting accelerations in three orthogonal axes is suitably used as the movement detection device 72.

A state determination unit 56 of the second embodiment determines whether or not the subject is in a sleep state according to analyze a pulse rate H identified by a pulse analysis unit 44 and a detection result by the movement detection device 72. More specifically, the state determination unit 56 determines that the subject is in the sleep state when the pulse rate H is lower than a predetermined threshold value and a state in which the movement detection device 72 does not detect a body movement of the subject continues for a predetermined time period. The state determination unit 56 determines that the subject is in an awake state, in a case where the pulse rate H is lower than the predetermined threshold but the body movement of the subject is detected and the body movement of the subject is not detected but the pulse rate H exceeds the predetermined threshold value.

In the second embodiment, the same effect as the first embodiment is also realized. Further, in the second embodiment, since the detection result of the movement detection device 72 is reflected in a determination of an active state of the subject, as compared with a configuration in which only the pulse rate H is used for the determination of the active state, there is an advantage that the active state of the subject can be estimated with high accuracy.

In FIG. 6, both the pulse rate H identified by the pulse analysis unit 44 and the detection result by the movement detection device 72 are used for determining the active state of the subject, however, the use of the pulse rate H can be omitted. That is, it is also possible to use only the detection result of the movement detection device 72 for determining the active state. For example, when the state in which the movement detection device 72 does not detect the body movement of the subject continues for a predetermined time, the state determination unit 56 determines that the subject is in the sleep state.

Third Embodiment

FIG. 7 is a configuration diagram focused on a function of a blood pressure measurement device 100 in a third embodiment. As illustrated in FIG. 7, the blood pressure measurement device 100 of the third embodiment has a configuration in which the state determination unit 56 of the first embodiment is replaced with an environment determination unit 58 and a temperature and humidity detection device 74 is added. The temperature and humidity detection device 74 is an environmental sensor that repeatedly detects temperature or humidity of an environment where a subject is present (hereinafter referred to as "measurement environment") at a predetermined cycle, and is configured to include, for example, a temperature sensor and a humidity sensor. The measurement environment can also be said to be an environment in which the blood pressure measurement device 100 is used. The environment determination unit 58 in FIG. 7 determines whether there is a change in the temperature or humidity of the measurement environment. Specifically, the environment determination unit 58 of the third embodiment determines whether there is a change according to whether or not a time change rate of the temperature or humidity exceeds a threshold value. Both temperature and humidity can be taken into consideration.

In a case where the temperature or humidity of the measurement environment where the subject is present suddenly fluctuates, there is a possibility that the blood pressure P of the subject suddenly fluctuates. For example, when the temperature suddenly drops, the blood pressure P of the subject may increase due to contraction of the blood vessel. Also, for example, when the humidity suddenly rises in a high temperature environment, the blood pressure P of the subject may decrease due to a heat stroke. Therefore, in a case where the temperature or the humidity of the measurement environment fluctuates, it is desirable to raise a measurement frequency of the blood pressure P as compared with a situation where the temperature or the humidity is stable. In consideration of the above circumstances, a measurement control unit 62 of the third embodiment shortens a measurement interval d of the blood pressure P in a case where the environment determination unit 58 determines that there is a change in the temperature or humidity of the measurement environment and a change determination unit 54 determines that a time change rate δ of the blood pressure P exceeds a threshold value δTH.

FIG. 8 is a flowchart of a measurement control processing in the third embodiment. As illustrated in FIG. 8, step SB1 of the measurement control processing (FIG. 5) of the first embodiment is replaced with step SC in the third embodiment. Upon starting the measurement control processing, the environment determination unit 58 determines whether or not the temperature or humidity of the measurement environment suddenly fluctuates (SC). When the temperature or humidity suddenly fluctuates (SC: YES) and the time change rate δ of the blood pressure P exceeds the threshold value δTH (SB2: YES), the measurement control unit 62 shortens the measurement interval d to the interval d2 (SB3), and a notification processing unit 64 notifies of the abnormal state of the subject (SB4). On the other hand, when the fluctuation in temperature or humidity of the measurement environment is not observed (SC: NO), if the blood pressure P is a numerical value outside a normal range N (SB6: NO), the shortening of the measurement interval d (SB3) and the notification of the abnormal state (SB4) are executed.

As described above, in the third embodiment, the blood pressure P is identified by analysis of the detection signal D in which a light that passed through the measurement region M of the subject is detected. Therefore, as in the first embodiment, it is possible to reduce the physical load of the subject compared with the technology of PTL 1 that uses a cuff to measure the blood pressure. Also, when the temperature or humidity of the measurement environment fluctuates, the measurement interval d of the blood pressure P is shortened. Therefore, it is possible to appropriately detect the blood pressure fluctuation in a situation where there is a high possibility that the blood pressure P of the subject fluctuates. Further, as in the first embodiment, compared with a configuration in which the blood pressure P is identified at the interval d2 irrespective of the condition of the subject, there is an advantage that a processing load of a control device (in particular, a blood pressure analysis unit 42) is reduced.

In the third embodiment, since the measurement interval d is shortened also when the blood pressure P of the subject is not within the normal range N, as in the first embodiment, an effect that the blood pressure fluctuation can be appropriately detected in a situation where there is a possibility that the health condition of the subject is abnormal, is especially remarkable. In addition, when the temperature or humidity of the measurement environment suddenly fluctuates and when the blood pressure P is not within the normal range N, the abnormal state of the subject is notified. Therefore, it is possible to grasp the abnormal state of the subject at an early stage and to perform measures for improvement.

MODIFICATION EXAMPLE

Each embodiment exemplified above can be variously modified. It is also possible to combine two or more arbitrarily selected aspects from the above embodiments and the following examples as appropriate.

(1) As illustrated in FIG. 9, waveforms of a blood flow wave B1 in a normal temperature (average temperature) environment and a blood flow wave B2 in a low temperature environment are different. Taking the above tendency into consideration, in the third embodiment, it is also possible to use an indicator calculated from the blood flow wave B (detection signal D) as an indicator of a drop in temperature in the measurement environment (hereinafter referred to as "temperature indicator"). Specifically, an environment determination unit 58 determines whether there is a sudden drop in temperature according to the temperature indicator identified from a detection signal D, instead of a temperature detected by a temperature and humidity detection device 74. According to the above configuration, since the temperature and humidity detection device 74 can be omitted, there is an advantage that the configuration of a blood pressure measurement device 100 is simplified. However, it is also possible to detect a sudden drop in temperature by using the temperature indicator together with the temperature detected by the temperature and humidity detection device 74.

Specific examples of the temperature indicator usable for detecting the drop in temperature are exemplified below. A symbol Qs in FIG. 9 means a maximum value of a blood flow rate Q within one cycle of the blood flow wave B, and a symbol Qd means a minimum value of the blood flow rate Q within one cycle of the blood flow wave B. A symbol Qave means an average value of the blood flow rate Q within one cycle of the blood flow wave B and a symbol Qp is the blood flow rate Q derived from a pulse wave component reflected upstream side from an end of a blood vessel. A symbol ΔT means a time length of a peak of the blood flow wave B.

[a] Maximum Value Qs, Fluctuation Range (Qs-Qd), Pulsatility Index, Resistance Index When the temperature of the measurement environment drops, peripheral blood vessel contracts and the blood flow rate Q (for example, the maximum value Qs) decreases. Therefore, it is possible to use the maximum value Qs within one cycle of the blood flow wave B as the temperature indicator. For example, in a case where a reduction rate of the maximum value Qs (decrease amount per unit time) exceeds a threshold value, the environment determination unit 58 determines that the temperature of the measurement environment is suddenly dropped.

Since the fluctuation range (Qs-Qd), the pulsatility index (PI), and the resistance index (RI) of the blood flow rate Q of the subject also tend to decrease in conjunction with the temperature of the measurement environment, it can be used as the temperature indicator like the maximum value Qs. The pulsatility index is a numerical value ((Qs-Qd)/Qave) obtained by dividing the fluctuation range (Qs-Qd) of the blood flow rate Q by the average value Qave and the resistance index is a numerical value ((Qs-Qd)/Qs) obtained by dividing the fluctuation range (Qs-Qd) of the blood flow rate Q by the maximum value Qs.

[b] Reflectance, Time Length ΔT

The numerical value (Qp-Qd)/(Qs-Qd) obtained by dividing the difference (Qp-Qd) between the reflected flow rate Qp and the minimum value Qd by the fluctuation range (Qs-Qd) of the blood flow rate Q is an indicator (reflectance) of a degree of reflection of the pulse wave component to the upstream side from the end of the blood vessel. As the temperature of the measurement environment drops, the reflection of the pulse wave component is promoted by the contraction of the peripheral blood vessel, so the reflectance increases. Therefore, it is possible to use the reflectance as a temperature indicator. Specifically, in a case where the increase rate of the reflectance (increase amount per unit time) exceeds the threshold value, the environment determination unit 58 determines that the temperature of the measurement environment is suddenly dropped. The time length ΔT of the peak of the blood flow wave B also has a tendency to increase when the temperature of the measurement environment is dropped, so it can be used as a temperature index like the reflectance.

[c] Pulse Wave Velocity V, Blood Vessel Cross Sectional Area A

When the temperature of the measurement environment drops, the blood vessel becomes difficult to deform, so that the pulse wave velocity V tends to rise. In addition, as the temperature of the measurement environment drops, the peripheral blood vessel contracts and the blood in the artery stays, and as a result, the blood vessel cross sectional area A of the artery tends to rise. Therefore, the pulse wave velocity V and the blood vessel cross sectional area A can also be used as a temperature indicator. Specifically, in a case where an increasing rate of the pulse wave velocity V or the blood vessel cross sectional area A exceeds the threshold value, the environment determination unit 58 determines that the temperature of the measurement environment is suddenly dropped.

(2) In each of the above described embodiments, the blood pressure P of the subject is displayed on the display device 24, however, the measurement result notified to the user is not limited to the numerical value of the blood pressure P itself. For example, it is also possible that a blood pressure state (high blood pressure/normal/low blood pressure) from the blood pressure P identified by a blood pressure analysis unit 42 is determined and a notification processing unit 64 causes a display device 24 to display the detection result. In addition, it is also possible that the notification processing unit 64 causes the display device 24 to display the active state (for example, sleep state/awake state/exercise state) of the subject determined by a state determination unit 56.

(3) It is also possible to combine from the first embodiment to the third embodiment mutually. For example, a blood pressure measurement device 100 including both the state determination unit 56 of the first embodiment or the second embodiment and the environment determination unit 58 of the third embodiment is also supposed. In at least one of a case where the state determination unit 56 determines that the subject is in a sleep state and a case where the environment determination unit 58 determines that the temperature or humidity of the measurement environment fluctuates, a measurement control unit 62 shortens the measurement interval d to the interval d2 when the time change rate δ of the blood pressure P exceeds the threshold value δTH.

(4) In each of the above described embodiments, each biological information (blood pressure P, blood vessel cross sectional area A, pulse wave velocity V) is calculated by the arithmetic operation of the equation (for example, equation (1) or equation (2)), the method of identifying the biological information is not limited to the above examples. Specifically, it is assumed that the biological information is identified using a table stored in advance in a storage device 22. For example, from the table that associates each numerical value of the blood vessel cross sectional area A and the pulse wave velocity V with each numerical value of the blood pressure P, the blood pressure analysis unit 42 is able to search for the blood pressure P corresponding to the numerical values of the blood vessel cross sectional area A and the pulse wave velocity V.

(5) In each of the above described embodiments, the measurement interval d is set to either the standard interval d1 or the interval d2, however, the measurement interval d is not limited to the two values. For example, in the first embodiment or the second embodiment, it is also possible to shorten the measurement interval d in multiple stages as the time, during which the time change rate δ exceeds the threshold value δTH in the sleep state, is longer. Further, in the third embodiment, it is also possible to change the measurement interval d in multiple stages according to the time change rate of the temperature or humidity of the measurement environment (for example, the measurement interval d is set to a shorter time as the time change rate is larger).

(6) In each of the above described embodiments, the detection signal D is generated by detecting the light passed through the measurement region M, however, it is also possible to generate the detection signal D by detecting a sound wave such as an ultrasonic wave. Specifically, an irradiation unit 32 of the detection device irradiates the measurement region M with a sound wave such as an ultrasonic wave, and a detection unit 34 generates the detection signal D by detecting the sound wave that passed through the measurement region M. As understood from the above description, the irradiation unit 32 is included as an element for irradiating the measurement region M of the subject with the measurement wave, and the detection unit 34 is included as an element for detecting the measurement wave that passed through the measurement region M and generates the detection signal D. The measurement wave is a wave motion including a light wave and a sound wave.

(7) In each of the above described embodiments, the blood pressure measurement device 100 that can be attached on the wrist of the subject is exemplified, however, a specific form (mounting position) of the blood pressure measurement device is arbitrary. For example, any type of blood pressure measurement device can be adapted such as a patch type that can be attached to a body of the subject, an earring type that can be attached to an auricle of the subject, a finger mounted type (for example, a claw type) that can be attached to a fingertip of the subject, a head mounted type that can be attached on the head of the subject. However, in a state where the blood pressure measurement device such as a finger mounted type is attached, it is assumed that there can be a problem with daily life, so from a viewpoint of constantly measuring the blood pressure P without interruption in daily life, the blood pressure measurement device 100 of each of the above described types that can be attached on the wrist of the subject is particularly preferable. Note that, the blood pressure measurement device in a form of being attached (externally attached) to various electronic equipment such as a wristwatch can also be realized.

(8) In each of the above described embodiments, the configuration in which the blood pressure measurement device 100 includes the storage device 22 and the display device 24 has been exemplified, however, it is also possible to make the storage device 22 or the display device 24 a device separate from the blood pressure measurement device 100. For example, it is also possible to install the storage device 22 or the display device 24 in a terminal device (for example, a portable phone or a smart phone) capable of communicating with the blood pressure measurement device 100.

(9) The preferred embodiment of the present invention is also grasped as a movement method (blood pressure measurement method) of the blood pressure measurement device 100 according to each of the above described embodiments. In the blood pressure measuring method corresponding to the first embodiment or the second embodiment, the blood pressure measurement device 100 shortens the interval d for identifying the blood pressure P, when the blood pressure P of the subject is repeatedly identified by analyzing the detection signal D in which the measurement wave that has passed through the measurement region M of the subject is detected, when it is determined whether or not the subject is in a sleep state, when it is determined whether or not the time change rate δ of the blood pressure P exceeds the threshold value δTH, when it is determined that the subject is in a sleep state, and when it is determined that the time change rate δ exceeds the threshold value δTH. In the blood pressure measuring method corresponding to the third embodiment, the blood pressure measurement device 100 shortens the interval d for identifying the blood pressure P, when the blood pressure P of the subject is repeatedly identified by analyzing the detection signal D in which the measurement wave that has passed through the measurement region M of the subject is detected, when it is determined that whether or not there is a change in the temperature or humidity of the measurement environment where the subject is present, when it is determined whether or not the time change rate δ of the blood pressure P exceeds the threshold value δTH, when it is determined that there is a change in the temperature or humidity of the measurement environment, and when it is determined that the time change rate δ exceeds the threshold value δTH.

(10) As described above, the blood pressure measurement device 100 exemplified in each of the above embodiments is realized by cooperation of the control device 20 and a program. A program corresponding to the first embodiment or the second embodiment causes a computer to function as the blood pressure analysis unit 42 that repeatedly identifies the blood pressure P of the subject by analyzing the detection signal D in which the measurement wave that has passed through the measurement region M of the subject is detected, the state determination unit 56 that determines whether or not the subject is in a sleep state, the change determination unit 54 that determines whether or not the time change rate δ of the blood pressure P exceeds the threshold value δTH, and the measurement control unit 62 that shortens the interval d where the blood pressure analysis unit 42 identifies the blood pressure P, when the state determination unit 56 determines that the subject is in a sleep state, and when the change determination unit 54 determines that the time change rate δ exceeds the threshold value δTH. A program corresponding to the third embodiment causes a computer to function as the blood pressure analysis unit 42 that repeatedly identifies the blood pressure P of the subject by analyzing the detection signal D in which the measurement wave that has passed through the measurement region M of the subject is detected, the environment determination unit 58 that determines whether there is a change in temperature or humidity of a measurement environment in which the subject is present, the change determination unit 54 that determines whether or not the time change rate δ of the blood pressure P exceeds the threshold value δTH, and the measurement control unit 62 that shortens the interval d where the blood pressure analysis unit 42 identifies the blood pressure P, when the environment determination unit 58 determines that there is a change in temperature or humidity of a measurement environment in which the subject is present, and when the change determination unit 54 determines that the time change rate δ exceeds the threshold value δTH.

The programs exemplified above may be provided in a form stored in a computer readable storage medium and installed in the computer. The storage medium is, for example, a non-transitory storage medium, and an optical storage medium (optical disc) such as a CD-ROM is a good example, and also a storage medium of any known type such as a semiconductor storage medium or a magnetic storage medium may be included. Further, the programs exemplified above can also be provided as an application program installable in a terminal device (for example, portable phone or smart phone) capable of communicating with the blood pressure measurement device 100.

REFERENCE SIGNS LIST

100 . . . blood pressure measurement device
12 . . . casing unit
14 . . . belt
20 . . . control device
22 . . . storage device
24 . . . display device
26 . . . detection device
32 . . . irradiation unit
322 . . . light emitter
324 . . . drive circuit
34 . . . detection unit
342 . . . light receiver
344 . . . A/D converter
42 . . . blood pressure analysis unit
42, 421 . . . first arithmetic operation unit
422 . . . second arithmetic operation unit
44 . . . pulse analysis unit
52 . . . blood pressure determination unit
54 . . . change determination unit
56 . . . state determination unit
58 . . . environment determination unit
62 . . . measurement control unit
64 . . . notification processing unit
72 . . . movement detection device
74 . . . temperature and humidity detection device

The invention claimed is:

1. A blood pressure measurement device for measuring a blood pressure of a subject, the blood pressure measurement device comprising:
a light sensor configured to measure a measurement wave that passes through a measurement region of the subject and generate a detection signal; and
a processor programmed to:
repeatedly identify the blood pressure of the subject by analyzing the detection signal;
determine whether or not the subject is in a sleep state or an awake state;
determine whether or not a time change rate of the blood pressure exceeds a threshold value;
shorten a standard interval in which the light sensor measures the blood pressure in a case where the subject is determined as being in the sleep state and the time change rate exceeds the threshold value; and
maintain a standard interval in which the light sensor measures the blood pressure in a case where the subject is determined as being in the awake state even when the time change rate exceeds the threshold value.

2. The blood pressure measurement device according to claim 1, wherein
the processor is further programmed to:
identify a pulse rate according to the detection signal, and
determine whether or not the subject is in the sleep state according to the identified pulse rate.

3. The blood pressure measurement device according to claim 1, further comprising:
a movement sensor that detects a movement of the subject,
wherein the processor determines whether or not the subject is in the sleep state according to a detection result by the movement sensor.

4. The blood pressure measurement device according to claim 1, wherein
the processor is further programmed to:
determine whether or not the blood pressure is within a normal range, and
shorten a time interval where the processor identifies the blood pressure in a case where the blood pressure is determined as not being within the normal range.

5. The blood pressure measurement device according to claim 4, wherein
the processor is further programmed to:
output a notification of an abnormal state of the subject in a case where the processor determines that the blood pressure is not within the normal range.

6. A blood pressure measurement method for measuring a blood pressure of a subject, the method comprising:
measuring, by a light sensor, a measurement wave that passes through a measurement region of the subject;
generating, by the light sensor, a detection signal based on the measured measurement wave;
identifying repeatedly, by a processor, the blood pressure of the subject by analyzing the generated detection signal;
determining, by the processor, whether or not the subject is in a sleep state or an awake state;
determining, by the processor, whether or not a time change rate of the blood pressure exceeds a threshold value;
shortening, by the processor, a standard interval in which the light sensor measures the blood pressure in a case where the subject is determined as being in the sleep state and the time change rate exceeds the threshold value; and
maintaining, by the processor, the standard interval in which the light sensor measures the blood pressure in a case where the subject is determined as being in the awake state even when the time change rate exceeds the threshold value.

7. The blood pressure measurement device according to claim 2, further comprising:
a movement sensor configured to detect a movement of the subject, wherein
wherein the processor determines whether or not the subject is in the sleep state according to a detection result by the movement sensor.

8. The blood pressure measurement device according to claim 2, wherein
the processor is further programmed to:
determine whether or not the blood pressure is within a normal range, and
shorten a time interval where the processor identifies the blood pressure in a case where the processor determines that the blood pressure is not within the normal range.

9. The blood pressure measurement device according to claim 3, wherein
the processor is further programmed to:
determine whether or not the blood pressure is within a normal range, and
shorten a time interval where the processor identifies the blood pressure in a case where the processor determines that the blood pressure is not within the normal range.

10. The blood pressure measurement device according to claim 7, wherein
the processor is further programmed to:
determine whether or not the blood pressure is within a normal range, and
shorten a time interval where the processor identifies the blood pressure in a case where the processor determines that the blood pressure is not within the normal range.

11. The blood pressure measurement device according to claim 8, wherein
the processor is further programmed to:
output a notification of an abnormal state of the subject in a case where the processor determines that the blood pressure is not within the normal range.

12. The blood pressure measurement device according to claim 9, wherein
the processor is further programmed to:
output a notification of an abnormal state of the subject in a case where the processor determines that the blood pressure is not within the normal range.

13. The blood pressure measurement device according to claim 10, wherein
the processor is further programmed to:
output a notification of an abnormal state of the subject in a case where the processor determines that the blood pressure is not within the normal range.

\* \* \* \* \*